United States Patent [19]

Kisida et al.

[11] Patent Number: 4,486,449
[45] Date of Patent: Dec. 4, 1984

[54] THIOCARBAMATE COMPOUNDS, AND THEIR USE

[75] Inventors: Hirosi Kisida, Hyogo; Makoto Hatakoshi, Osaka, both of Japan

[73] Assignee: Sumitomo Chemical Company, Limited, Osaka, Japan

[21] Appl. No.: 397,894

[22] Filed: Jul. 13, 1982

[30] Foreign Application Priority Data

Jul. 31, 1981 [JP] Japan .................................. 56-121229
Jan. 11, 1982 [JP] Japan .................................... 57-3186
Feb. 16, 1982 [JP] Japan ................................... 57-24079
Mar. 27, 1982 [JP] Japan ................................... 57-49399

[51] Int. Cl.³ ..................... C07C 155/02; A01N 47/10
[52] U.S. Cl. ................................ 424/300; 260/455 A; 71/3; 71/DIG. 1
[58] Field of Search .................... 260/455 A; 424/300

[56] References Cited

U.S. PATENT DOCUMENTS

| | | | |
|---|---|---|---|
| 3,904,662 | 9/1975 | Henrick et al. | 260/455 A |
| 3,912,815 | 10/1975 | Henrick et al. | 260/455 A |
| 4,060,629 | 11/1977 | Karrer | 260/455 A |
| 4,080,470 | 3/1978 | Karrer | 260/455 A |
| 4,215,139 | 7/1980 | Fischer et al. | 260/455 A |

FOREIGN PATENT DOCUMENTS 2848656 of 1979 Fed. Rep. of Germany ... 260/455 A
1368267 of 1974 United Kingdom ........... 260/455 A

OTHER PUBLICATIONS

Reid, Organic Chemistry of Bivalent Sulfur, vol. IV, Chem. Pub. Co., Inc., 1962, p. 198, 199 & 201.

*Primary Examiner*—Henry R. Jiles
*Assistant Examiner*—Robert C. Whittenbaugh
*Attorney, Agent, or Firm*—Birch, Stewart, Kolasch & Birch

[57] ABSTRACT

A thiolcarbamate compound of the formula:

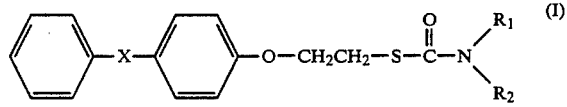

wherein X is an oxygen atom, a sulfur atom or a methylene group, $R_1$ is a hydrogen atom, a $C_1$-$C_4$ alkyl group or a $C_3$-$C_4$ alkenyl group and $R_2$ is a $C_1$-$C_4$ alkyl group, a $C_3$-$C_4$ alkenyl group, a $C_3$-$C_4$ alkynyl group or a cyclopropyl group, which is useful as an insect controlling agent.

16 Claims, No Drawings

THIOCARBAMATE COMPOUNDS, AND THEIR USE

The invention relates to thiolcarbamate compounds, and their production and use.

The thiolcarbamate compounds are representable by the formula:

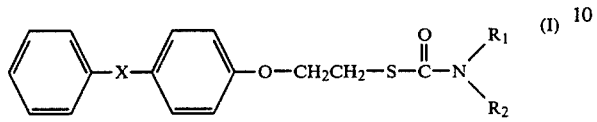
(I)

wherein X is an oxygen atom, a sulfur atom or a methylene group, $R_1$ is a hydrogen atom, a $C_1$–$C_4$ alkyl group or a $C_3$–$C_4$ alkenyl group and $R_2$ is a $C_1$–$C_4$ alkyl group, a $C_3$–$C_4$ alkenyl group, a $C_3$–$C_4$ alkynyl group or a cyclopropyl group.

In the above significances, the alkyl group, the alkenyl group and the alkynyl group may be straight or branched. Specific examples of those groups include methyl, ethyl, n-propyl, iso-propyl, n-butyl, iso-butyl, sec-butyl, t-butyl, allyl, propargyl, etc.

Among the thiolcarbamate compounds (I), preferred are those wherein X is an oxygen atom, $R_1$ is a hydrogen atom or a methyl group and $R_2$ is a methyl group or an ethyl group.

It is known that some thiolcarbamate compounds have insecticidal and acaricidal activities against larvae of shield bug (Pentatomidae), two spotted spider mite (*Tetranychus urticae*), common red spider (*Tetranychus telarius*), etc. (DT-OS 2,848,656).

As a result of an extensive study, it has been found that the thiolcarbamate compounds (I) are useful for the control of insects. Their utility as insect control agents is believed to be attributable to their juvenile hormone-like activity. In fact, they exert an excellent juvenile hormone-like controlling activity against larvae of common mosquito (*Culex pipiens pallens*), yellow fever mosquito (*Aedes aegypti*), housefly (*Musca domestica*), etc. The thiolcarbamate compounds (I) are preferably applied to the immature insects, i.e. during the embryo, larvae or pupae stage, in view of their effect on metamorphosis and otherwise cause abnormal development leading to death or inablility to reproduce.

The thiolcarbamate compounds (I) can be prepared by various procedures, of which some typical ones are shown below.

Procedure A

A halide of the formula:

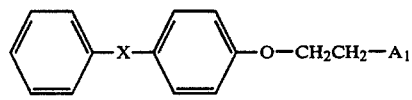
(II)

wherein $A_1$ is a halogen atom and X is as defined above is reacted with a thiolcarbamate salt of the formula:

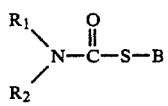
(III)

wherein B is an alkali metal atom or a quaternary ammonium group and $R_1$ and $R_2$ are each as defined above in an inert solvent (e.g. water, acetone, toluene, tetrahydrofuran, N,N-dimethylformamide, dimethylsulfoxide, methanol, ethanol) at a temperature of −30° to 100° C. for a period of 0.5 to 20 hours to give the thiolcarbamate compound (I). The molar ratio of the halide (II) and the thiolcarbamate salt (III) may be usually 1:1–3, preferably 1:1.1–1.2.

Procedure B

A thiolhaloformate of the formula:

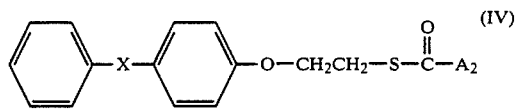
(IV)

wherein $A_2$ is a halogen atom and X is as defined above is reacted with an amine of the formula:

(V)

wherein $R_1$ and $R_2$ are each as defined above in the presence of an acid eliminating agent such as an alkali metal hydroxide (e.g. sodium hydroxide, potasium hydroxide) or an organic base (e.g. pyridine, triethylamine) in an inert solvent (e.g. water, acetone, toluene, tetrahydrofuran, N,N-dimethylformamide, dimethylsulfoxide, methanol, ethanol) at a temperature of −30° to 100° C. for a period of 0.5 to 20 hours to give the thiolcarbamate compound (I). The molar ratio of the thiolhaloformate (IV) and the amine (V) may be usually 1:1–3, preferably 1:1.1–1.2.

Procedure C

A thiol of the formula:

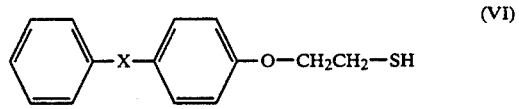
(VI)

wherein X is as defined above is reacted with a carbamoyl halide of the formula:

(VII)

wherein $A_3$ is a halogen atom, $R_3$ is a $C_1$–$C_4$ alkyl group or a $C_3$–$C_4$ alkenyl group and $R_2$ is as defined above in the presence of a base such as an alkali metal hydroxide (e.g. sodium hydroxide, potassium hydroxide) or an organic base (e.g. pyridine, triethylamine) in an inert solvent (e.g. water, acetone, toluene, tetrahydrofuran, N,N-dimethylformamide, dimethylsulfoxide, methanol, ethanol) at a temperature of −30° to 100° C. for a period of 0.5 to 20 hours to give the thiolcarbamate compound (I: $R_1=a$ $C_1$–$C_4$ alkyl group or a $C_3$–$C_4$ alkenyl group). The molar ratio of the thiol (VI) and the carbamoyl halide (VII) may be usually 1:1-3, preferably 1:1.1-1.2.

Procedure D

A thiol of the formula:

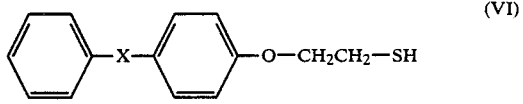

(VI)

wherein X is as defined above is reacted with an isocyanate of the formula:

$R_2-N=C=O$ (VIII)

wherein $R_2$ is as defined above in the presence or absence of a base such as an alkali metal hydroxide (e.g. sodium hydroxide, potassium hydroxide) or an organic base (e.g. pyridine, triethylamine) in an inert solvent (e.g. acetone, toluene, tetrahydrofuran, N,N-dimethylformamide, dimethylsulfoxide) at a temperature of $-30°$ to $100°$ C. for a period of 0.5 to 50 hours to give the thiolcarbamate compound (I:$R_1$=H). The molar ratio of the thiol (VI) and the isocyanate (VIII) may be usually 1:1-3, preferably 1:1.1-1.2.

In the above procedures, the recovery of the produced thiolcarbamate compound (I) from the reaction mixture and the purification of the recovered thiolcarbamate compound (I) may be carried out per se conventional procedures. For instance, the purification can be achieved by chromatography, distillation, etc.

The starting compounds (II), (III), (IV), (V), (VI), (VII), and (VIII) used in the above procedures are known or can be produced by conventional procedures as described in the following literatures: DT-OS 2,616,755; Org. Synth., Coll. Vol. I, 435 (1941); Org. Synth., Coll. Vol. II, 358 (1943); Ber. Deut. Chem. Ges., 63, 888 (1930); Ber. Deut. Chem. Ges., 56, 320 (1923); Synthesis, 1974, 811; Recl. Trav. Chim. Pays-Bas, 53, 1101 (1934); Can. J. Chem., 34, 1093 (1956).

Some practical embodiments of the procedures for preparation of the thiolcarbamate compound (I) are shown in the following Examples.

EXAMPLE 1

(Production of Compound No. 1 according to Procedure (A))

Into a mixture of tetrahydrofuran (30 ml), a 40% aqueous solution of methylamine (0.48 g; $6.14 \times 10^{-3}$ mol) and sodium methoxide (0.33 g; $6.14 \times 10^{-3}$ mol), carbonylsulfide gas was gradually introduced at a temperature below 5° C. until saturation. The resulting mixture was stirred at room temperature (ca. 20° C.) for 1 hour. Then, a solution of 2-(4-phenoxy)phenoxyethyl bromide (1.50 g; $5.12 \times 10^{-3}$ mol) in tetrahydrofuran (10 ml) was dropwise added thereto at room temperature in about 30 minutes. After the dropwise addition was completed, the resultant mixture was stirred at room temperature overnight. The reaction mixture was concentrated, water (50 ml) was added thereto, and the resulting mixture was extracted with ether (50 ml) twice. The ether extract was washed with water, dried over anhydrous sodium sulfate and concentrated. The resulting oily product was subjected to column chromatography using silica gel (50 g) and methylene chloride as a developing solvent to give S-2-(4-phenoxy)phenoxyethyl-N-methylthiolcarbamate (0.75 g) as white crystals. Yield, 48.0%. M.P., 90°-91° C.

IR (nujol): 3350, 1655 cm$^{-1}$.

NMR (CDCl$_3$) δ (ppm): 6.70-7.40 (m, 9 H), 5.47 (m, 1 H), 4.09 (t, 6 Hz, 2 H), 3.23 (t, 6 Hz, 2 H), 2.85 (w, 5 Hz, 3 H).

EXAMPLE 2

(Production of Compound No. 9 according to Procedure (B))

A solution of S-2-(4-phenoxy)phenoxyethanethiol chloroformate (3.09 g; 0.01 mol) in toluene (10 ml) was dropwise added to a solution of N-methyl-N-ethylamine (0.71 g; 0.012 mol) and triethylamine (1.21 g; 0.012 mol) in toluene (20 ml) at a temperature of $-20°$ to $-15°$ C. in 30 minutes. After the dropwise addition was completed, stirring was carried out at room temperature for 3 hours. The reaction mixture was washed with water, dried over anhydrous sodium sulfate and concentrated. The obtained oily product was subjected to column chromatography using silica gel (50 g) and methylene chloride as a developing solvent to give S-2-(4-phenoxy)phenoxyethyl-N-methyl-N-ethylthiolcarbamate (1.88 g) as a colorless, transparent liquid. Yield. 56.7%. $n_D^{25.0}$ 1.5801.

IR (neat): 1650 cm$^{-1}$.

NMR (CDCl$_3$) δ (ppm): 6.70-7.40 (m, 9 H), 4.00 (t, 6 Hz, 2 H), 3.05-3.55 (4 H), 2.83 (s, 3 H), 1.04 (t, 7 Hz, 3 H).

EXAMPLE 3

(Production of Compound No. 8 according to Procedure (C))

To a suspension of 62.9% sodium hydride (0.38 g; 0.01 mol) in dry tetrahydrofuran (30 ml), a solution of 2-(4-phenoxy)phenoxyethylmercaptan (2.46 g; 0.01 mol) in dry tetrahydrofuran (10 ml) was dropwise added at a temperature below 5° C. in 30 minutes while stirring. After the dropwise addition was completed, stirring was continued at room temperature for 1 hour. The resultant mixture was cooled below 5° C., a solution of N,N-dimethylcarbamoyl chloride (1.08 g; 0.01 mol) in dry tetrahydrofuran (10 ml) was dropwise added thereto in 30 minutes and the resulting mixture was stirred at room temperature overnight. The reaction mixture was concentrated, water (20 ml) was added thereto, and the resultant mixture was extracted with ether (30 ml) twice. The ether extract was washed with water, dried over anhydrous sodium sulfate and concentrated. The obtained oily product was subjected to column chromatography using silica gel (50 g) and methylene chloride as a developing solvent to give S-2-(4-phenoxy)phenoxyethyl-N,N-dimethylthiolcarbamate (2.49 g) as a colorless, transparent liquid. Yield, 78.5%. $n_D^{22.5}$ 1.5887. On allowing to stand at room temperature over a period of one week, the product was crystallied. M.P., 75°-76° C.

IR (neat): 1650 cm$^{-1}$.

NMR (CDCl$_3$) δ (ppm): 6.70-7.40 (m, 9 H), 4.10 (t, 6 Hz, 2 H), 3.26 (t, 6 Hz, 2 H), 2.94 (s, 6 H).

EXAMPLE 4

(Production of Compound No. 2 according to Procedure (D))

To a mixture of 2-(4-phenoxy)phenoxyethyl mercaptan (2.46 g; 0.01 mol) and triethylamine (1.01 g; 0.01 mol) in dry N,N-dimethylformamide (30 ml), ethyl isocyanate (0.85 g; 0.012 mol) was dropwise added at room temperature while stirring in 30 minutes, and the resultant mixture was allowed to stand at room temperature for 50 hours. Water (50 ml) was added to the reaction mixture, followed by extraction with ether (30 ml) twice. The extract was washed with water, dried over anhydrous sodium sulfate and concentrated. The obtained oily product was subjected to chromatography using silica gel (50 g) and methylene chloride as a developing solvent to give S-2-(4-phenoxy)phenoxyethyl-N-ethylthiolcarbamate (1.03 g) as white crystals. Yield, 32.6%. M.P., 89°–90° C.

IR (nujol): 3340, 1653 cm$^{-1}$.

NMR (CDCl$_3$) δ (ppm): 6.70–7.40 (m, 9 H), 5.47 (m, 1 H), 3.89 (t, 6 Hz, 2 H), 2.93–3.46 (4 H), 0.92 (t, 7 Hz, 3 H).

In the same manner as above, there were prepared the thiolcarbamate compounds (I), of which some examples are shown in Table 1.

TABLE 1

$$\text{Ph-X-C}_6\text{H}_4\text{-O-CH}_2\text{CH}_2\text{-S-C(=O)-N}\begin{pmatrix}R_1\\R_2\end{pmatrix}$$

| Compound No. | X | R$_1$ | R$_2$ | Physical property |
|---|---|---|---|---|
| 1 | O | H | CH$_3$ | M.P. 90–91° C. |
| 2 | O | H | C$_2$H$_5$ | M.P. 89–90° C. |
| 3 | O | H | n-C$_3$H$_7$ | M.P. 54–56° C. |
| 4 | O | H | iso-C$_3$H$_7$ | M.P. 115–116° C. |
| 5 | O | H | cyclo-C$_3$H$_5$ | M.P. 108–109° C. |
| 6 | O | H | n-C$_4$H$_9$ | M.P. 91–92° C. |
| 7 | O | H | CH$_2$=CH—CH$_2$— | M.P. 71–72° C. |
| 8 | O | CH$_3$ | CH$_3$ | M.P. 75–76° C. |
| 9 | O | CH$_3$ | C$_2$H$_5$ | $n_D^{25.0}$ 1.5801 |
| 10 | O | CH$_3$ | n-C$_3$H$_7$ | $n_D^{25.0}$ 1.5726 |
| 11 | O | CH$_3$ | CH≡C—CH$_2$— | $n_D^{25.5}$ 1.5740 |
| 12 | O | C$_2$H$_5$ | C$_2$H$_5$ | $n_D^{22.5}$ 1.5847 |
| 13 | O | n-C$_3$H$_7$ | n-C$_3$H$_7$ | $n_D^{25.5}$ 1.5634 |
| 14 | O | iso-C$_4$H$_9$ | iso-C$_4$H$_9$ | $n_D^{25.5}$ 1.5469 |
| 15 | O | CH$_2$=CH—CH$_2$— | CH$_2$=CH—CH$_2$— | $n_D^{25.5}$ 1.5767 |
| 16 | CH$_2$ | H | C$_2$H$_5$ | M.P. 109–110° C. |
| 17 | CH$_2$ | CH$_3$ | CH$_3$ | $n_D^{25.0}$ 1.5857 |
| 18 | CH$_2$ | CH$_3$ | C$_2$H$_5$ | $n_D^{25.0}$ 1.5785 |
| 19 | CH$_2$ | C$_2$H$_5$ | C$_2$H$_5$ | $n_D^{25.0}$ 1.5816 |
| 20 | S | H | C$_2$H$_5$ | $n_D^{24.0}$ 1.6482 |
| 21 | S | CH$_3$ | CH$_3$ | $n_D^{25.0}$ 1.6321 |

On the practical application as insect control agents, the thiolcarbamate compounds (I) may be used by themselves, but usually they are used in the form of an appropriate composition such as dusts, wettable powders, oil sprays, emulsifiable concentrates, tablets, granules, fine granules, aerosols and flowables. The above oil sprays or emulsifiable concentrate can be applied with or without dilution using ultra-low volume sprayers.

The content of the thiolcarbamate compound (I) in the composition may be from about 0.1 to 99% by weight, preferably from about 2 to 80% by weight.

The composition can be formulated in a per se conventional manner by mixing at least one of the thiolcabamate compounds (I) with an appropriate solid or liquid carrier(s) or diluent(s) with or without an appropriate adjuvant(s) (e.g. surfactants, adherents, dispersants, stabilizers) for improving the dispersibility and other properties of the active ingredient on use.

The composition can also be formulated in microcapsules, coated granulates, solutions in polymeric substances, etc., whereby the thiolcarbamate compound (I) is released at a fixed rate in a certain dosage.

Examples of the solid carriers or diluents are botanical materials (e.g. flour, tobacco stalk powder, soybean powder, walnut shell powder, wooden powder, saw dust, bran, bark powder, cellulose powder, vegetable extract residue), fibrous materials (e.g. paper, corrugated cardboard, old rags), synthesized plastic powders, clays (e.g. kaolin, bentonite, fuller's earth, pyrophyllite, sericite), talcs, other inorganic materials (e.g. hydrated silica, diatomaceous earth, pumice, sulfur powder, active carbon) and chemical fertilizers (e.g. ammonium sulfate, ammonium phosphate, ammonium nitrate, urea, ammonium chloride).

Examples of the liquid carriers or diluents are water, alcohols (e.g. methanol, ethanol), ketones (e.g. acetone, methyl ethyl ketone), ethers (e.g. diethyl ether, dioxane, cellosolve, tetrahydrofuran), aromatic hydrocarbons (e.g. benzene, toluene, xylene, methylnaphthalene), aliphatic hydrocarbons (e.g. gasoline, kerosene, lamp oil), esters, nitriles, acid amides (e.g. dimethylformamide, dimethylacetamide), halogenated hydrocarbons (e.g. dichloroethane, trichloroethylene, carbon tetrachloride, etc.

Examples of the surfactants are alkylsulfates, alkylsulfonates, alkylarylsulfonates, polyethylene glycol ethers, polyhydric alcohol esters, etc. Examples of the adherents and dispersants may include casein, gelatin, starch powder, carboxymethyl cellulose, gum arabic, alginic acid, ligninsulfonate, bentonite, molasses, polyvinyl alcohol, pine oil and agar. As the stabilizers, there may be used PAP (isopropyl acid phosphates mixture), TCP (tricresyl phosphate), tolu oil, epoxydized oil, various surfactants, various fatty acids and their esters, etc.

In addition, the said composition may contain insecticides, acaricides, nematocides, fungicides, herbicides, plant growth regulators, fertilizers, soil improvers, etc. Particularly when employed in conjuction with insect growth regulators and conventional insecticides, a broad spectrum of activity or a more immediate effect on very heterogeneous populations is provided. Examples of the insect growth regulators include insect chitin synthesis inhibitors (e.g. N-(4-chlorophenylaminocarbonyl)-2,6-di-fluorobenzamide) and other juvenile hormone active substances (e.g. 1-(4'-ethylphenoxy)-6,7-epoxy-3,7-dimethyl-2- octene, 2-propinyl (2E,4E)-3,7,11-trimethyl-2,4-dodecadienoate). Examples of the insecticides include organic phosphorus compounds (e.g. fenitrothion (O,O-dimethyl-O-(3-methyl-4-nitrophenyl)phosphorothioate), malathion (S-[1,2-bis(ethoxycarbonyl)ethyl] O,O-dimethylphosphorothioate), dimethoate (O,O-dimethyl-S (N-methylcarbamoylmethyl)phosphorodithioate), salithion (2-methoxy-4H-1,3,2-benzdioxaphosphorin-2-sulfide), diazinon (O,O-diethyl-O-(2-isopropyl-6-methyl-4-pyrimydinyl)phosphorothioate), dipterex (2,2,2-trichloro-1-hydroxyethyl-O,O-dimethylphosphonate), dichlorvos (O-(2,2-dichlorovinyl)-O,O-dimethylphosphate), etc.), carbamate compounds (e.g. MPMC(3,4-dimethylphenyl N-methylcarbamate), MTMC (m-tolyl N-methylcarbamate), BPMC (2-sec-butylphenyl N-methylcarbamate), carbaryl (1-naphthyl N-methylcarbamate), etc.) and pyrethroid compounds (e.g. permethrin (3-phenoxybenzyl-d,1-cis,trans-3-(2,2-dichlorovinyl)-2,2-dimethylcyclopropanecarboxylate), fenvalerate (α-cyano-m-phenoxybenzyl α-isopropyl-p-chlorophenylacetate, etc.).

Some practical embodiments of the composition for the control of insects according to the invention are illustratively shown in the following Formulation Examples wherein % and part (s) are by weight.

FORMULATION EXAMPLE 1

Each of Compound Nos. 1 to 21 (20 parts), an emulsifier (a mixture of polyoxyethylene-styrenated phenyl ether, polyoxyethylene-styrenated phenyl ether polymer and an alkylarylsulfonate) (20 parts) and xylene (60 parts) are mixed well to make an emulsifiable concentrate containing the active ingredient in a concentration of 20%.

FORMULATION EXAMPLE 2

Each of Compound Nos. 1 to 21 (20 parts) and an emulsifier (sodium laurylsulfate) (5 parts) are mixed well, and diatomaceous earth (300 mesh) (75 parts) is added thereto, and the resultant mixture is mixed well in a pulverizer to make a wettable powder containing the active ingredient in a concentration of 20%.

FORMULATION EXAMPLE 3

Each of Compound Nos. 1 to 21 (3 parts) is dissolved in acetone (20 parts), talc (300 mesh) (97 parts) is added thereto, and the resultant mixture is mixed well in a pulverizer. Then, acetone is eliminated by evaporation to give a dust containing the active ingredient in a concentration of 3%.

FORMULATION EXAMPLE 4

Each of Compound Nos. 1 to 21 (5 parts), a dispersant (calcium ligninsulfonate) (2 parts) and kaolin (93 parts) are mixed well in a pulverizer. To the resultant mixture, water is added in an amount of 10%, and the resulting mixture is kneaded well and granulated by the aid of a granulator, followed by drying to give granules containing the active ingredient in a concentration of 5%.

FORMULATION EXAMPLE 5

Each of Compounds Nos. 1 to 21 (2 parts), a dispersant (calcium lingninsulfonate) (2 parts) and kaolin (96 parts) are mixed well in a pulverizer. Water is added to the resultant mixture in an amount of 10%. The resulting mixture is mixed well and granulated by the aid of a granulator. The granules are dried to give fine granules containing the active ingredient in a concentration of 2%.

The thiolcarbamate compounds (I) show a juvenile hormone-like controlling effect against various insects belonging to Hemiptera, Lepidoptera, Coleoptera, Diptera, Orthoptera, Dictyoptera, etc. and numerous pests belonging to Acarina in low concentrations and therefore can be used for the control of various harmful insects in agricultural fields, forest lands, granaries, sanitary facilities, etc. The thiolcarbamate compounds (I) are also suitable as additives to the feed of silkworms and can be used in silkworm farming to improve the quality and quantity of the silk thread. Specific examples of the harmful insects and other pests are as follows:

1. Hemiptera:
    smaller brown planthopper (*Laodelphax striatellus*), brown planthopper (*Nilaparvata lugens*), white-backed planthopper (*Sogatella furcifera*), green rice leafhopper (*Nephotettix cincticeps*), rice stink bug (*Lagynotomus elongatus*), common green stink bug (*Nezara aantennata*), white-spotted bug (*Eysarcaris ventralis*), green peach aphid (*Myzus persicae*), cotton aphid (*Aphis gossypii*), cabbage aphid (*Brevicoryne brassicae*), cottony cushion scale (*Icerya purchasi*), citrus mealy bug (*Planococcus citri*), arrowhead scale (*Unaspis yanonensis*), etc.

2. Lepidoptera:
    tobacco cutworm (*Spodoptera litura*), rice stem border (*Chilo suppressalis*), grass leaf roller (*Cnaphalocrocis medinalis*), wax moth (*Galleria mellonella*), diamond back moth (*Pluttella xylostella*), smaller tea tortrix (*Adoxophyes sp.*), common white (*Pieris rapae*), cabbage armyworm (*Mamestra brassicae*), armyworm (*Pseudaletia separate*), etc.

3. Coleoptera:
    varied carpet beetle (*Anthrenus verbasci*), lyctus powder-post beetle (*Lyctus brunneus*), rice leaf beetle (*Onlema oryzae*), rice plant weevil (*Echinocnemus squameus*), 28-spotted lady beetle (*Henosepilachna vigintioctopunctata*), cupreous beetle (*Anomala cuprea*), japanese beetle (*Polilla japonica*), etc.

4. Diptera:
    housefly (*Musca domestica*), melon fly (*Dacus cucurbitae*), common mosquito (*Culex pipiens pallens*), yellow fever mosquito (*Aedes aegypti*), malaria mosquito (Anopheles sp.), etc.

5. Orthoptera:
    short-winged rice grasshopper (*Oxya yezoensis*), etc.

6. Dictyoptera:
    German cockroach (*Blattella germanical*), smoky brown cockroach (*Periplaneta fuliginosa*), etc.

7. Acarina:
    carmine mite (*Tetranychus cinnabarinus*), etc. The following Examples show some typical test data indicating the excellent insect control activity of the thiolcarbamate compounds (I). The compounds used for comparison are as follows:

| Compound No. | Chemical structure | Remarks |
|---|---|---|
| A | (diphenyl ether with O-(CH2)n-SCN(=O)(CH3)2 group) | DT-OS 2,848,656 |
| B | (diphenylmethane with O-(CH2)n-SCN(=O)(CH3)2 group) | DT-OS 2,848,656 |
| C | (methoxy ester chain structure) | U.S. Pat. Nos. 3,904,662 and 3,912,815 |
| D | (phenoxyphenyl ethyl ester structure) | U.S. Pat. No. 3,824,274 |

TEST EXAMPLE 1

Pupae of wax moth (*Galleria mellonella*) were collected within 20 hours from the pupation. According to the Schneiderman's method (J. Insect Physiol., 11, 1641 (1965)), a puncture of about 1 mm$^2$ was made in the right side of the thoracic dorsum of each pupa, and the wound was sealed with a designed amount of the test compound dissolved in a mixture of paraffin wax and peanut oil. The medicated pupae were kept at 28° C. The pupal cuticule at the medicated part was peeled off before emergence, and observation was made to examine the formation of the pupal cuticule, from which the average rate of reaction to the test compound was determined, and the dose of the test compound for 50% inhibition of the metamorphosis (ID$_{50}$) was calculated. The results are shown in Table 2.

TABLE 2

| Test compound No. | ID$_{50}$ (μg/pupa) |
|---|---|
| 1 | <1 |
| 2 | <1 |
| 8 | <0.21 |
| 9 | <1 |
| 12 | <0.1 |
| 17 | <1 |
| 21 | <1 |
| A | 67 |
| B | >67 |
| C | 2.2 |

TEST EXAMPLE 2

An emulsion prepared according to Formulation Example 1 was diluted with water to make a 400 fold dilution. The dilution (0.7 ml) was added to 100 ml of distilled water. Last instar larvae of common mosquito (*Culex pipiens pallens*) were released therein and reared until their emergence. The rate of emergence was observed (two replications). The results are shown in Table 3.

TABLE 3

| Test compound No. | Concentration (ppm) | Rate of emergence (%) |
|---|---|---|
| 1 | 3.5 | 0 |

TABLE 3-continued

| Test compound No. | Concentration (ppm) | Rate of emergence (%) |
|---|---|---|
| 2 | 3.5 | 0 |
| 3 | 3.5 | 0 |
| 4 | 3.5 | 0 |
| 5 | 3.5 | 0 |
| 6 | 3.5 | 0 |
| 7 | 3.5 | 0 |
| 8 | 3.5 | 0 |
| 9 | 3.5 | 0 |
| 10 | 3.5 | 0 |
| 11 | 3.5 | 0 |
| 12 | 3.5 | 0 |
| 13 | 3.5 | 0 |
| 14 | 3.5 | 0 |
| 15 | 3.5 | 0 |
| 16 | 3.5 | 0 |
| 17 | 3.5 | 0 |
| 18 | 3.5 | 0 |
| 19 | 3.5 | 0 |
| 20 | 3.5 | 0 |
| 21 | 3.5 | 0 |
| A | 3.5 | 0 |
| C | 3.5 | 0 |
| Untreated | — | 90 |

TEST EXAMPLE 3

An emulsion prepared according to Formulation Example 1 was diluted with water to a designed dilution. The dilution (0.5 ml) was added to 100 ml of distilled water. Twenty last instar larvae of common mosquito (*Culex pipiens pallens*) were released therein and reared until their emergence. The 50% emergence inhibition concentration (IC$_{50}$) was determined (two replications). The results are shown in Table 4.

TABLE 4

| Test Compound No. | IC$_{50}$ (ppm) |
|---|---|
| 1 | 0.0023 |
| 2 | 0.0023 |
| 3 | 0.008 |
| 4 | 0.009 |
| 5 | 0.004 |
| 8 | 0.0005 |
| 9 | 0.0003 |
| 12 | 0.002 |
| 13 | 0.02 |
| 15 | 0.02 |

TABLE 4-continued

| Test Compound No. | IC$_{50}$ (ppm) |
| --- | --- |
| 16 | 0.004 |
| 17 | 0.0004 |
| 19 | 0.005 |
| 21 | 0.006 |
| A | 0.063 |
| B | 0.14 |
| D | 0.03 |

TEST EXAMPLE 4

In the same manner as in Test Example 3 but rearing yellow fever mosquito (*Aedes aegypti*) instead of common mosquito (*Culex pipiens pallens*), and the 50% emergence inhibition concentration (IC$_{50}$) was examined (two replications). The results are shown in Table 5.

TABLE 5

| Test Compound No. | IC$_{50}$ (ppm) |
| --- | --- |
| 1 | 0.0004 |
| 2 | 0.0005 |
| 8 | 0.0004 |
| 9 | 0.0004 |
| A | 0.28 |
| B | ≑1 |

TEST EXAMPLE 5

Powdered animal feed (2 g) were thoroughly mixed with bran (14 g). An emulsion prepared according to Formulation Example 1 and diluted with water to a designed concentration was added thereto. The resultant mixture was stirred well to make an artificial culture. Fourty 5-day-old larvae of housefly (*Musca domestica*) were reared therein until their pupation. The obtained pupae were placed into a plastic cup, and the rate of emergence was determined. According to the following equation, the emergence inhibition (%) was calculated:

Emergence inhibition (%) =

$$\left(1 - \frac{\text{Rate of emergence in treated plot}}{\text{Rate of emergence in untreated plot}}\right) \times 100$$

The results are shown in Table 6.

TABLE 6

| Test compound No. | Emergence inhibition (%) | | |
| --- | --- | --- | --- |
| | 100 ppm | 30 ppm | 10 ppm |
| 1 | 85 | 25 | 0 |
| 2 | 83 | 18 | — |
| 8 | 100 | 93 | 65 |
| 9 | 100 | 85 | 10 |
| A | 10 | 0 | — |
| B | 0 | — | — |

What is claimed is:

1. A thiolcarbamate compound of the formula:

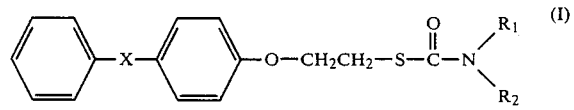

wherein X is an oxygen atom, a sulfur atom or a methylene group, R$_1$ is a hydrogen atom, a C$_1$-C$_4$ alkyl group or a C$_3$-C$_4$ alkenyl group and R$_2$ is a C$_1$-C$_4$ alkyl group, a C$_3$-C$_4$ alkenyl group, a C$_3$-C$_4$ alkynyl group or a cyclopropyl group.

2. The compound according to claim 1, wherein X is an oxygen atom, R$_1$ is a hydrogen atom or a methyl group and R$_2$ is a methyl group or an ethyl group.

3. The compound according to claim 1, wherein X is an oxygen atom and R$_1$ and R$_2$ are each a methyl group.

4. The compound according to claim 1, wherein X is an oxygen atom, R$_1$ is a methyl group and R$_2$ is an ethyl group.

5. The compound according to claim 1, wherein X is an oxygen atom, R$_1$ is a hydrogen atom and R$_2$ is a methyl group.

6. The compound according to claim 1, wherein X is an oxygen atom, R$_1$ is a hydrogen atom and R$_2$ is an ethyl group.

7. A composition for the control of insects which comprises an insecticidally effective amount of at least one thiolcarbamate compound of the formula:

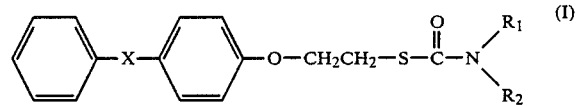

wherein X is an oxygen atom, a sulfur atom or a methylene group, R$_1$ is a hydrogen atom, a C$_1$-C$_4$ alkyl group or a C$_3$-C$_4$ alkenyl group and R$_2$ is a C$_1$-C$_4$ alkyl group, a C$_3$-C$_4$ alkenyl group, a C$_3$-C$_4$ alkynyl grup or a cyclopropyl group for the control of insects as an active ingredient, and an inert carrier or diluent.

8. The composition according to claim 7, wherein the content of the active ingredient is from 0.1 to 99% by weight.

9. A method for controlling insects which comprises treating said insects with an insecticidally effective amount of at least one thiolcarbamate compound of the formula:

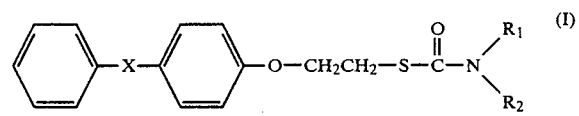

wherein X is an oxygen atom, a sulfur atom or a methylene group, R$_1$ is a hydrogen atom, a C$_1$-C$_4$ alkyl group or a C$_3$-C$_4$ alkenyl group and R$_2$ is a C$_1$-C$_4$ alkyl group, a C$_3$-C$_4$ alkenyl group, a C$_3$-C$_4$ alkynyl group or a cyclopropyl group for the control of said insects.

10. The method according to claim 9, wherein the insects are selected from the group consisting of Hemiptera, Lepidoptera, Coleoptera, Diptera, Orthoptera and Dictyoptera.

11. The method according to claim 9, wherein the insects are larvae of common mosquito (*Culex pipiens pallens*), yellow fever mosquito (*Aedes aegypti*) or housefly (*Musca domestica*).

12. The method according to claim 9, wherein x is an oxygen atom, R$_1$ is a hydrogen atom or a methyl group and R$_2$ is a methyl group or an ethyl group.

13. The method according to claim 9, wherein X is an oxygen atom and R$_1$ and R$_2$ are each a methyl group.

14. The method according to claim 9, wherein X is an oxygen atom, $R_1$ is a methyl group and $R_2$ is an ethyl group.

15. The method according to claim 9, wherein X is an oxygen atom, $R_1$ is a hydrogen atom and $R_2$ is a methyl group.

16. The method according to claim 9, wherein X is an oxygen atom, $R_1$ is a hydrogen atom and $R_2$ is an ethyl group.

* * * * *